United States Patent
Gurmarnik

Patent Number: 5,584,820
Date of Patent: Dec. 17, 1996

[54] SET FOR SPINAL ANESTHESIA

[76] Inventor: Simon Gurmarnik, 5 Hagen Rd., Newton Center, Mass. 02159

[21] Appl. No.: 519,459

[22] Filed: Aug. 25, 1995

[51] Int. Cl.⁶ ................................... A61M 5/00
[52] U.S. Cl. ............ 604/264; 604/158; 604/272
[58] Field of Search ................. 604/158, 160, 604/272, 21, 264, 273

[56] References Cited

U.S. PATENT DOCUMENTS

| | | | |
|---|---|---|---|
| 2,702,037 | 2/1955 | Walter | 604/272 |
| 2,828,744 | 4/1958 | Hirsch et al. | 604/272 X |
| 3,093,134 | 6/1963 | Roehr | 604/272 |
| 4,846,799 | 7/1989 | Tanaka et al. | 604/158 |
| 4,911,691 | 3/1990 | Aniuk et al. | 604/158 X |
| 4,969,875 | 11/1990 | Ichikawa et al. | 604/158 X |
| 5,306,239 | 4/1994 | Gurmarnik et al. | 604/158 X |
| 5,312,375 | 5/1994 | Gurmarnik | 604/272 X |

Primary Examiner—Sam Rimell
Attorney, Agent, or Firm—Ilya Zborovsky

[57] ABSTRACT

A set for spinal anesthesia has a hollow introducer needle, a spinal needle introducible through the introducer needle into subarachnoid space, and a separate elongated hollow fixing element having a first portion which is fixable with the introducer needle, and a second portion surrounding exclusively the spinal needle and fixable with the spinal needle, so that the spinal needle is movable through the means between a plurality of positions and is fixed by the second portion to the fixing element in each of the positions.

6 Claims, 1 Drawing Sheet 5,584,820

SET FOR SPINAL ANESTHESIA

BACKGROUND OF THE INVENTION

The present invention relates to a set for spinal anesthesia.

More particularly, it relates to a set which includes an introducer needle, a spinal needle and a stylet.

Sets for spinal anesthesia of the above mentioned type are known in the art. Usually, during the operation a big bore introducer needle is placed within intraspinal muscles. Then a small bore spinal needle is placed within the introducer needle to prevent its bending and curving, advanced further, and positioned within the subarachnoid space. The stylet which extends through the spinal needle is removed and after the cerebral spinal fluid appears, a syringe with anesthetic is attached to the spinal needle and medicine is injected. In this set, however, the spinal needle positioned through the introducer needle within the subarachnoid space is very unstable. It slides back and forth via the introducer needle.

In my U.S. Pat. No. 5,312,375 it has been proposed to provide means for removably fixing the spinal needle and the introducer needle with one another when the spinal needle enters the subarachnoid space so that the spinal needle is freely movable inside the introducer needle between a plurality of locations, and the means for removably fixing the spinal needle and the introducer needle engages the spinal needle and the introducer needle transversely to the direction of elongation in any of a plurality of positions. Therefore the spinal needle and the introducer needle are fixed with one another in any of a plurality of positions. While this proposal is very efficient, its disadvantage is that the modification of the introducer needle so as to provide in it the corresponding fixing means makes the introducer needle more expensive.

SUMMARY OF THE INVENTION

Accordingly, it is an object of the present invention to provide a set for spinal anesthesia, which avoids the disadvantages of the prior art.

In keeping with these objects and with others which will become apparent hereinafter, one feature of the present invention resides, briefly stated, in a set for spinal anesthesia which has a hollow introducer needle; a spinal needle introducible through the introducer needle into subarachnoid space; a stylet extendable through the spinal needle; and an additional elongated hollow fixing element having a first hollow portion extending into the interior of the introducer needle and a second hollow portion extending longitudinally from the first hollow portion over the spinal needle only and provided with means for fixing the second portion to the spinal needle, so that the spinal needle is freely longitudinally movable inside the introducer needle and the fixing element between a plurality of positions and can be fixed in any of the positions by the fixing means extending transversely to the needles.

When the set is designed in accordance with the present invention, the introducer needle and the spinal needle are not changed, but the additional fixing element is provided which engages in the spinal needle and engages in the introducer needle and is fixed with the spinal needle by the transversely extending fixing means in any desired position.

The novel features which are considered as characteristic for the invention are set forth in particular in the appended claims. The invention itself, however, both as to its construction and its method of operation, together with additional objects and advantages thereof, will be best understood from the following description of specific embodiments when read in connection with the accompanying drawings.

BRIEF DESCRIPTION OF THE DRAWINGS

The single FIGURE of the drawings is a view showing a set for spinal anesthesia in accordance with the present invention.

DESCRIPTION OF THE PREFERRED EMBODIMENTS

Figure 1:
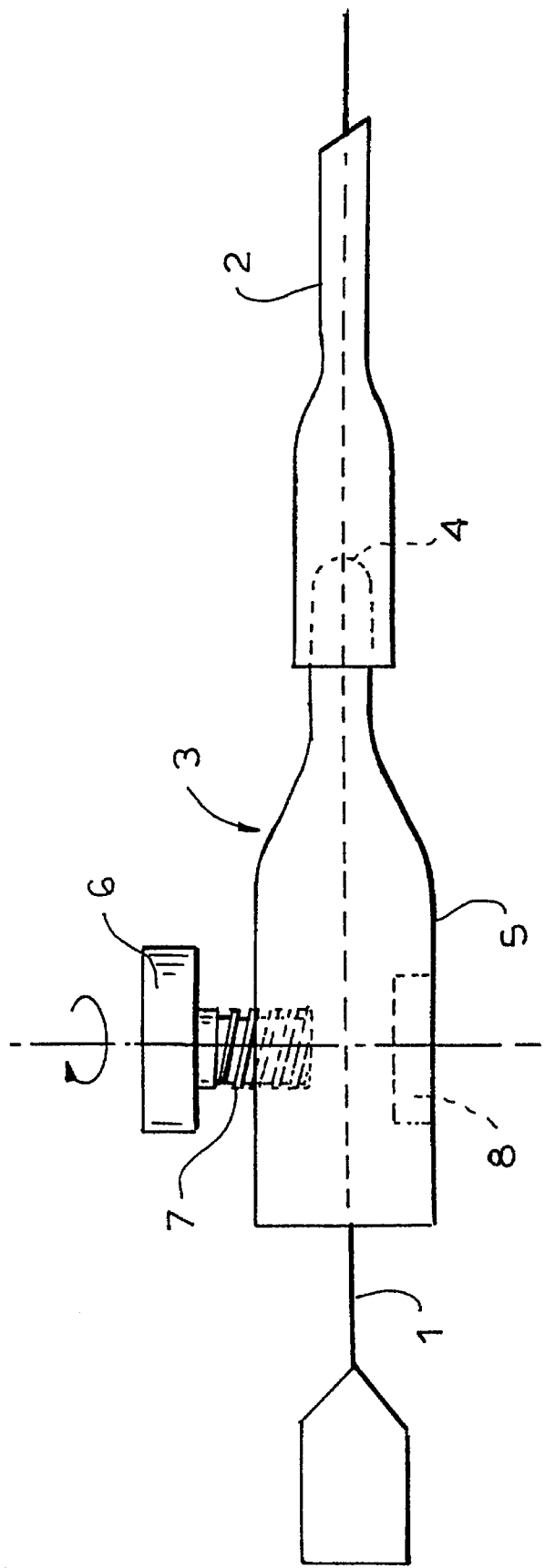

A set for spinal anesthesia in accordance with the present invention has a spinal needle which is identified with reference numeral 1. The spinal needle 1 is hollow and a not shown stylet extends through its interior. The set further has a hollow introducer needle which is identified with reference numeral 2. The spinal needle 1 extends through the introducer needle 2 as shown in the drawings.

The set is further provided with an additional elongated hollow fixing element which is identified as a whole with reference numeral 3. The fixing element 3 has a first longitudinal portion 4 which extends into an interior of the introducer needle 2. The portion 4 can be fixed to the introducer needle 2 by elastic action. The fixing element 3 can be composed of an elastic material; when the portion 4 is introduced into the interior of the rear end of the introducer needle 2, it is somewhat compressed and presses against the inner wall of the introducer needle 2 so as to be retained in the latter.

The additional fixing element 3 has a second portion 5 which exclusively surrounds the spinal needle 1. Fixing means are provided in the second portion 5. The fixing means include a screw 6 which extends through a threaded lateral opening 7 in the wall of the second portion 5. An elastic insert 8 is arranged inside the second portion 5 of the fixing element 3 at the opposite side of the spinal needle 1.

The set in accordance with the present invention operates in the following manner:

The introducer needle 2 is placed within the intraspinal muscle in stable position. Then the spinal needle 1 is placed within the introducer needle 2 to prevent bending and curving, is further advanced through an epidural space into the subarachnoid space. The stylet is removed from the spinal needle 1 and cerebral spinal fluid appears. After this, the screw 6 is tightened and the spinal needle 1 becomes fixed against the rubber insert 8 with respect to the fixing element 3, while the fixing element 3 is fixed with respect to the introducer needle 2. The spinal needle, the fixing element, and the introducer needle thereby form a rigid, fixed structure. Then, the syringe with anesthetic is attached to the spinal needle and medicine can be injected.

It will be understood that each of the elements described above, or two or more together, may also find a useful application in other types of constructions differing from the types described above.

While the invention has been illustrated and described as embodied in a set for spinal anesthesia, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. A set for spinal anesthesia, comprising a hollows introducer needle; a spinal needle introducible through said introducer needle into subarachnoid space; and an elongated hollow fixing element having a first portion which is fixable with said introducer needle, and a second portion surrounding exclusively said spinal needle and fixable with said spinal needle, so that the spinal needle is movable through said fixing element between a plurality of positions and is fixed by said second portion to said fixing element in each of said positions, said first portion being elastic so that it is retained in said introducer needle by elastic action.

2. A set for spinal anesthesia as defined in claim 1, wherein said first portion is formed as a portion insertable into the interior of a rear end of said introducer needle.

3. A set for spinal anesthesia as defined in claim 1, wherein said second portion is provided with means for fixing said second portion to said spinal needle, said fixing means extending transversely to a direction of elongation of said spinal needle.

4. A set for spinal anesthesia as defined in claim 3, wherein said fixing means includes a threaded hole provided in a wall of said second portion of said fixing element, and a screw extending through said threaded hole and pressing against said spinal needle.

5. A set for spinal anesthesia as defined in claim 4; and further comprising an elastic element arranged in said second portion of said fixing element opposite to said screw at an opposite side of said spinal needle.

6. A set for spinal anesthesia as defined in claim 1, wherein said first portion and said second portion are of one piece with one another so that said fixing element is a one piece element.

\* \* \* \* \*